US012544522B2

(12) United States Patent
Ishizeki et al.

(10) Patent No.: US 12,544,522 B2
(45) Date of Patent: Feb. 10, 2026

(54) MEDICAL AGENT INHALER

(71) Applicant: Tokico System Solutions, Ltd., Kanagawa (JP)

(72) Inventors: Kazunori Ishizeki, Kawasaki (JP); Shigemi Nakamura, Kawasaki (JP)

(73) Assignee: TOKICO SYSTEM SOLUTIONS, LTD., Kanagawa (JP)

( * ) Notice: Subject to any disclaimer, the term of this patent is extended or adjusted under 35 U.S.C. 154(b) by 633 days.

(21) Appl. No.: 17/927,230

(22) PCT Filed: Jun. 23, 2021

(86) PCT No.: PCT/JP2021/023709

§ 371 (c)(1),
(2) Date: Nov. 22, 2022

(87) PCT Pub. No.: WO2022/044514

PCT Pub. Date: Mar. 3, 2022

(65) Prior Publication Data

US 2023/0218838 A1 Jul. 13, 2023

(30) Foreign Application Priority Data

Aug. 26, 2020 (JP) ................................ 2020-142781

(51) Int. Cl.
*A61M 15/00* (2006.01)

(52) U.S. Cl.
CPC .... *A61M 15/0063* (2014.02); *A61M 15/0021* (2014.02); *A61M 15/0086* (2013.01); *A61M 2202/064* (2013.01)

(58) Field of Classification Search
CPC .......... A61M 15/0063; A61M 15/0021; A61M 15/0086; A61M 2202/064; A61M 15/002; A61M 15/0005; A61M 2206/16
See application file for complete search history.

(56) References Cited

U.S. PATENT DOCUMENTS

2004/0244794 A1 12/2004 Richards
2009/0178676 A1 7/2009 Villax et al.
(Continued)

FOREIGN PATENT DOCUMENTS

EP 1062962 12/2000
EP 1106196 A2 6/2001
(Continued)

OTHER PUBLICATIONS

Supplementary European Search Report received in European Patent Application No. EP 21860944.4, dated Aug. 12, 2024.
(Continued)

*Primary Examiner* — Elliot S Ruddie
(74) *Attorney, Agent, or Firm* — GREENBLUM & BERNSTEIN, P.L.C.

(57) ABSTRACT

A medical agent inhaler includes a body that is provided therein with a container accommodating chamber, a tubular mouthpiece that protrudes upward from the body, an inhalation passage having a first end that is open to a container accommodating part and a second end that is open to an upper end of the mouthpiece, a container that is accommodated in the container accommodating part and is provided therein with a medical agent accommodating chamber of which an upper side is formed as an opening, the container being capable of switching positions between a dosing position where the opening of the medical agent accommodating chamber is communicated with the inhalation passage and a storage position where the opening is separated from the inhalation passage, and an inflow passage that is disposed on the body to be positioned closer to the upper side than the container accommodating part.

8 Claims, 5 Drawing Sheets

(56) References Cited

U.S. PATENT DOCUMENTS

| | | | |
|---|---|---|---|
| 2013/0047985 A1 | 2/2013 | Harris et al. | |
| 2018/0036497 A1* | 2/2018 | Ventura ............. | A61M 15/0045 |

FOREIGN PATENT DOCUMENTS

| | | |
|---|---|---|
| EP | 1106196 A3 | 1/2004 |
| JP | 2004-537377 | 12/2004 |
| JP | 2009-537199 | 10/2009 |
| JP | 2017-516518 | 6/2017 |
| WO | 2007/132217 | 11/2007 |
| WO | 2016/174393 | 11/2016 |

OTHER PUBLICATIONS

Search Report issued in International Patent Application No. PCT/JP2021/023709, dated Jul. 20, 2021.
Written Opinion (ISA/237) issued International Patent Application No. PCT/JP2021/023709, dated Jul. 20, 2021.
Written Opinion (IPEA/408) issued in International Patent Application No. PCT/JP2021/023709, dated Feb. 8, 2022.
English language translation of Written Opinion (ISA/237) issued International Patent Application No. PCT/JP2021/023709, dated Jul. 20, 2021.
English language translation of Written Opinion (IPEA/408) issued in International Patent Application No. PCT/JP2021/023709, dated Feb. 8, 2022.

* cited by examiner

MEDICAL AGENT INHALER

TECHNICAL FIELD

The present invention relates to medical agent inhalers suitable in use for administering powdered medical agents to a lung.

BACKGROUND ART

It is widely known that a treatment method for administering powdered medical agents to a lung is effective for treatment of, for example, asthma, a chronic obstructive lung disease (COPD) or the like. In recent years, the treatment method for administering the powdered medical agent to the lung has been used also for viral diseases represented by influenza.

A medical agent inhaler for inhaling medical agents from the mouth is used for these treatments. It is preferable that this medical agent inhaler is disposable for suppressing a risk of infection or the like, is easily operable (capable of inhaling) by anybody and is capable of inhaling medical agents in a state where the medical agents are dispersed.

The medical agent inhaler includes a body that is provided therein with a container accommodating part, a tubular mouthpiece that protrudes upward from an upper part of the body, an inhalation passage of which a first end is open to the container accommodating part and of which a second end is open to an upper end of the mouthpiece, and a container that is provided therein with a medical agent accommodating chamber and is accommodated in the container accommodating part, the container being capable of switching positions between a dosing position where the medical agent accommodating chamber is communicated with the inhalation passage and a storage position where an opening of the medical agent accommodating chamber is separated from the inhalation passage.

The medical agent accommodating part of the container is formed in a bottomed shape to be open on the upper side. The container is provided with an air hole formed thereon for inflow of air from an exterior into a bottom part of the medical agent accommodating part. In addition, the body is provided with another air hole formed thereon to be communicated with the air hole of the container in the dosing position. Thereby, when a patient inhales with holding the mouthpiece in the mouth, air flows into the medical agent accommodating part from the air hole of the body and the air hole of the container and with this air, the medical agents accommodated in the medical agent accommodating part are inhaled from the inhalation passage to the lung while dispersing the medical agents (Patent Documents 1 and 2).

PRIOR ART DOCUMENT

Patent Document

Patent Document 1: International Publication No. WO
Patent Document 2: International Publication No. WO 2016/174393

SUMMARY OF THE INVENTION

The medical agent inhaler according to Patent Documents 1 and 2 is so configured that air is made to flow thereinto from the lower side of the medical agent accommodating part and the air is inhaled together with medical agents from the upper side of the medical agent accommodating part.

Therefore, in a state where the container is disposed in the dosing position and the air hole of the container is communicated with the air hole of the body, there occurs a problem that the medical agent in the medical agent accommodating part slips out to an exterior through each of the air holes.

Therefore, it is considered that a passage area of the air hole is made small to prevent slippage of the medical agent. However, when the passage area of the air hole is made small, the air cannot be made to sufficiently flow into the medical agent accommodating part. As a result, the medical agents in the medical agent accommodating part cannot sufficiently be dispersed or the amount of the medical agents to be capable of being inhaled is made small, which poses a problem that an inhalation efficiency on the medical agent is lowered.

An object of an aspect of the present invention is to provide a medical agent inhaler that can prevent slippage of medical agents from a medical agent accommodating part and inhale the medical agent efficiently.

An aspect of the present invention is characterized by including a body that is provided therein with a container accommodating part, a tubular mouthpiece that protrudes upward from an upper part of the body, an inhalation passage of which a first end is open to the container accommodating part and of which a second end is open to an upper end of the mouthpiece, a container that is accommodated in the container accommodating part and is provided therein with a medical agent accommodating chamber of which a lower side is closed and of which an upper side is formed as an opening, the container being capable of switching positions between a dosing position where the opening of the medical agent accommodating chamber is communicated with the inhalation passage and a storage position where the opening of the medical agent accommodating chamber is separated from the inhalation passage, and an inflow passage that is disposed on the body to be positioned closer to the upper side than the container accommodating part, of which a first end is open to an exterior and of which a second end is open toward the opening of the medical agent accommodating chamber disposed in the dosing position.

According to the aspect of the present invention, the slippage of the medical agent from the medical agent accommodating part can be prevented and besides, the medical agent can be inhaled efficiently.

MODE FOR CARRYING OUT THE INVENTION

Hereinafter, medical agent inhalers according to embodiments of the present invention will be in detail explained according to the accompanying drawings.

Figure 1:
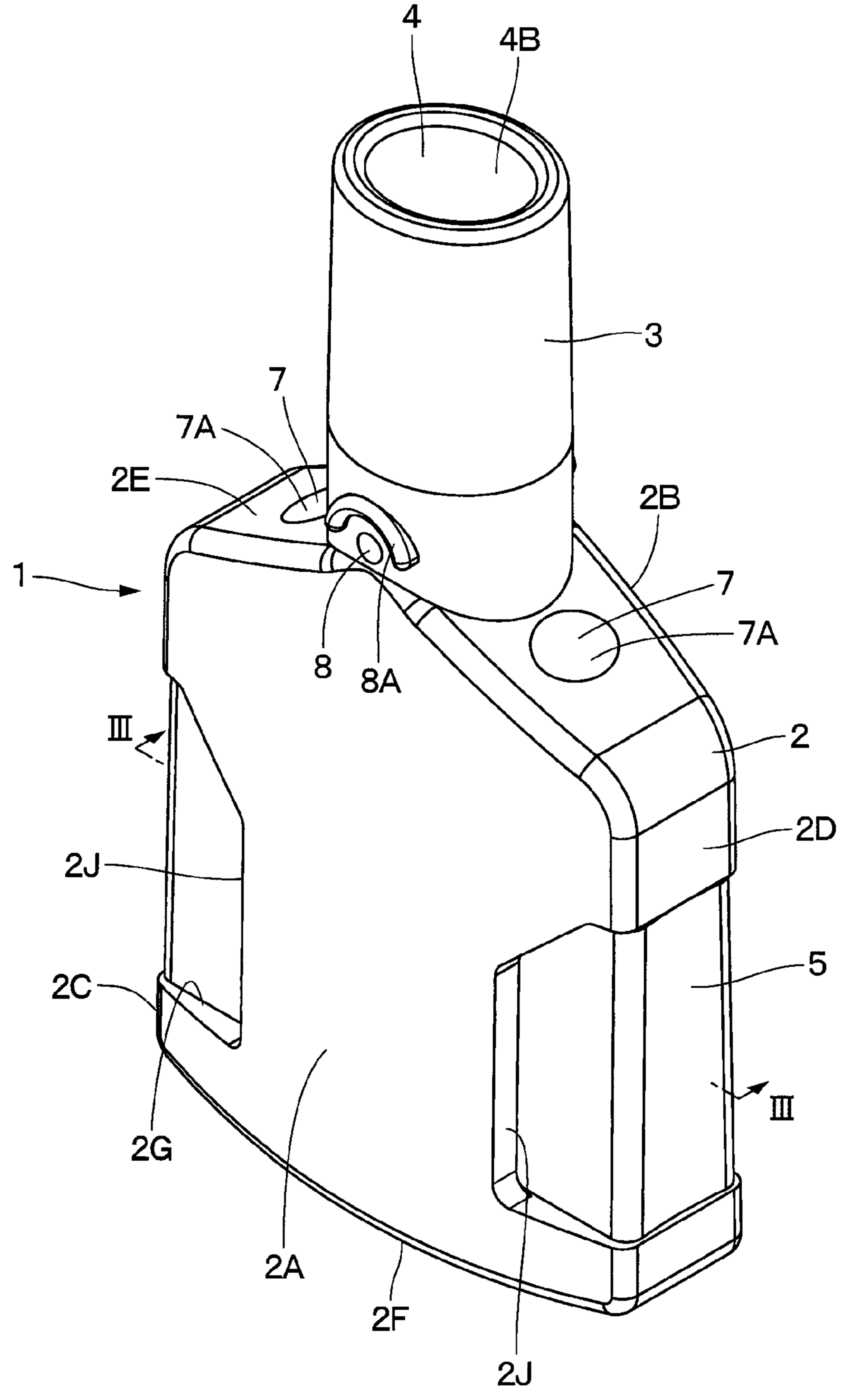
FIG. 1 is a perspective view showing a medical agent inhaler according to a first embodiment of the present invention.
Figure 2:
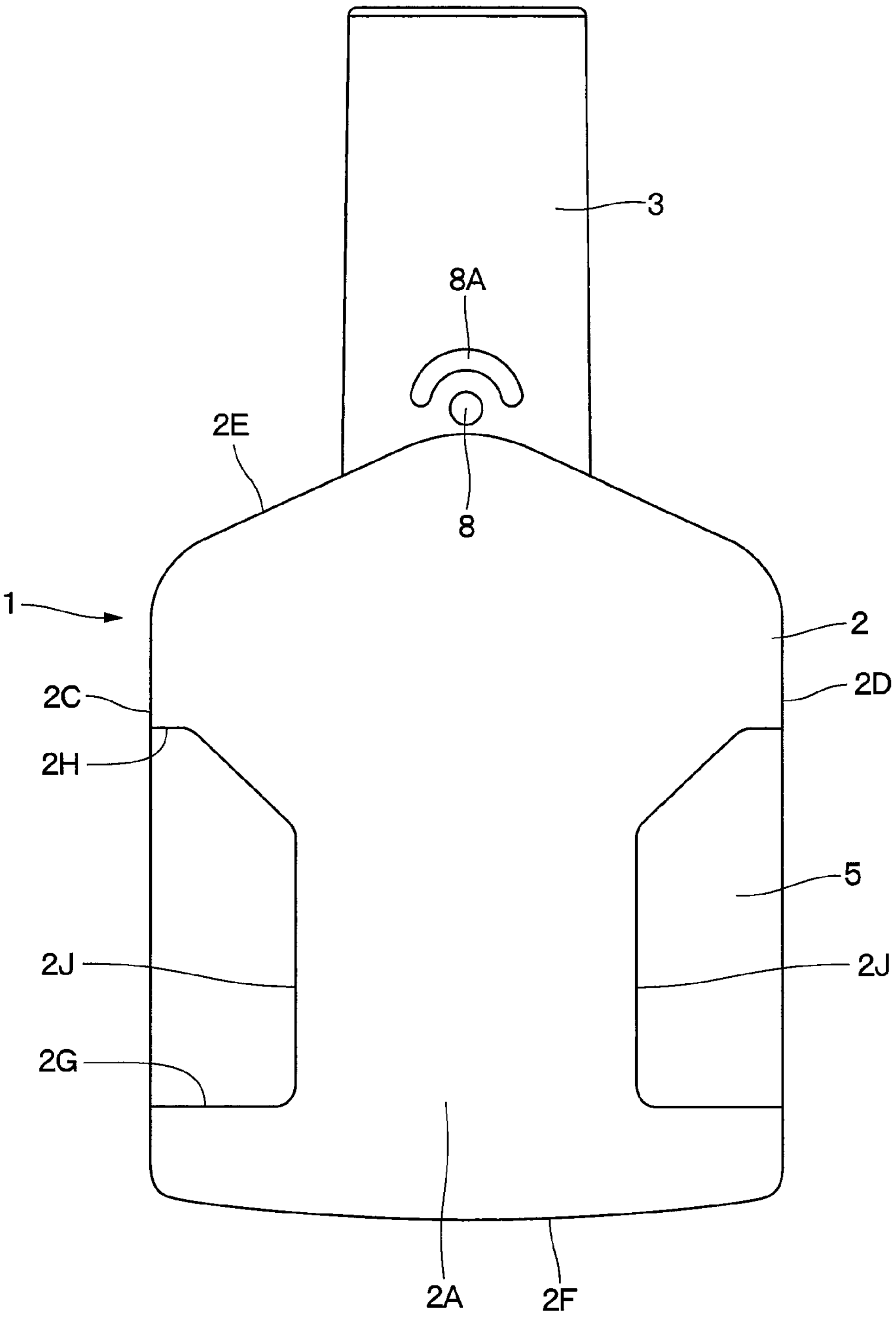
FIG. 2 is a front view showing the medical agent inhaler in FIG. 1.
Figure 3:
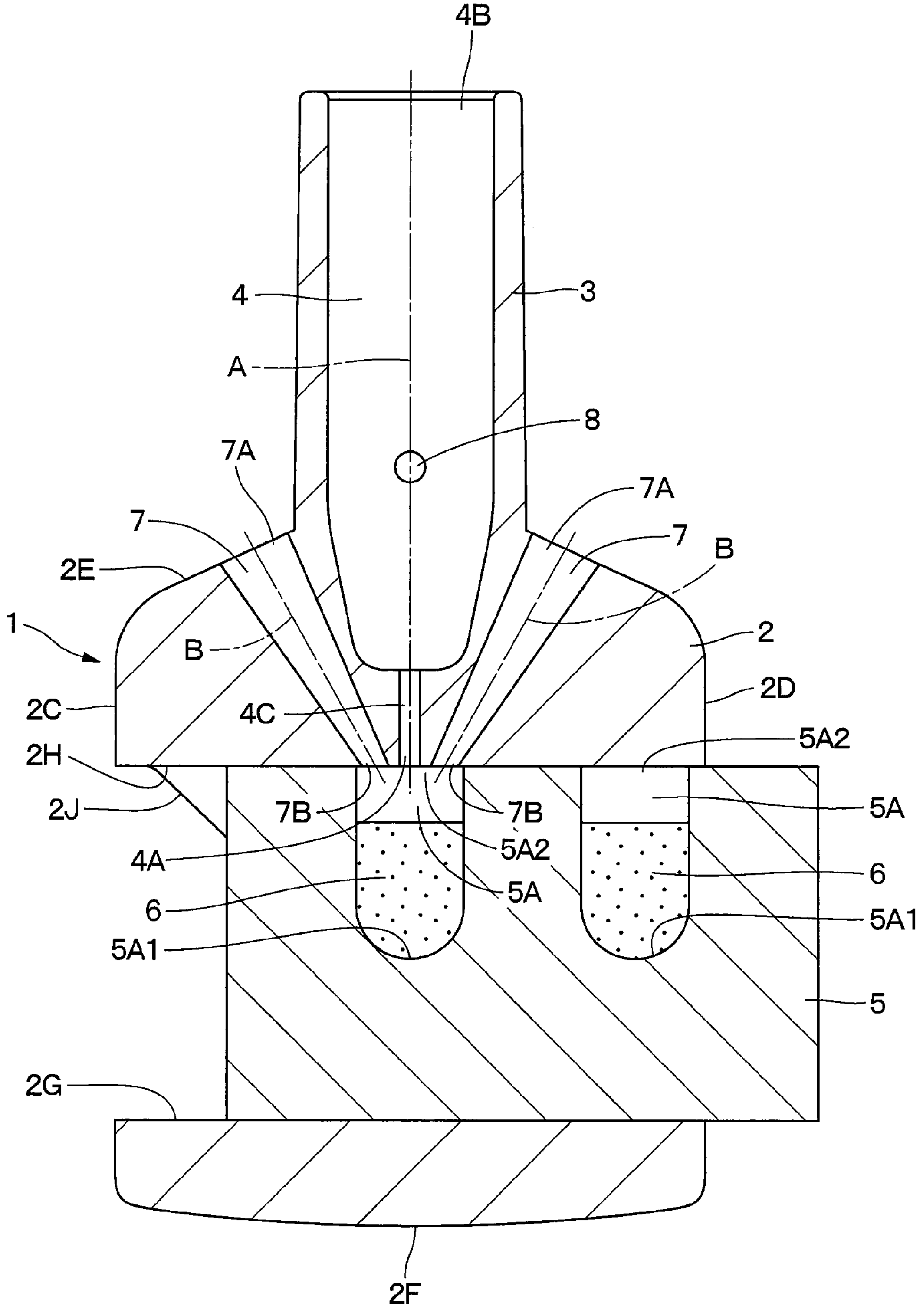
FIG. 3 is a cross section showing the medical agent inhaler, as viewed from an arrow III-III direction in FIG. 1.

FIGS. 1 to 3 show a first embodiment of the present invention. In FIGS. 1 and 2, a medical agent inhaler 1 according to the present embodiment administers powdered medical agents to a bronchus and a lung, for example. The medical agent inhaler 1 is used for treatment of, for example, asthma, a chronic obstructive lung disease (COPD), viral diseases and the like. The medical agent inhaler 1 includes a body 2, a mouthpiece 3, an inhalation passage 4, a container 5, and an inflow passage 7, which will be described later.

The body 2 is formed in a flat, rectangular shape in such a manner as to be easily gripped by hand at the time of inhaling medical agents 6 to be described later. Specifically, the body 2 has a front surface part 2A, a rear surface part 2B, a left surface part 2C, a right surface part 2D, an upper surface part 2E and a lower surface part 2F. On top of that, the body 2 is formed in the flat, rectangular shape in a front-back direction by disposing the front surface part 2A and the rear surface part 2B which face to each other, in positions close from each other.

The body 2 is provided therein with a container accommodating part 2G to accommodate the container 5 to be described later. As shown in FIG. 3, the container accommodating part 2G is positioned closer to the lower side from an intermediate part of the body 2 to be formed to penetrate in a left-right direction between the left surface part 2C and the right surface part 2D. In addition, the container accommodating part 2G is formed as a through hole (through space) in a flat, rectangular shape in the front-back direction for accommodating the container 5 in the flat, rectangular shape in the front-back direction to be movable in the left-right direction.

The inhalation passage 4 and the inflow passage 7 to be described later are open to a ceiling surface 2H of the container accommodating part 2G. Further, notch parts 2J in a C-letter shape are disposed in end parts in the left-right direction respectively, which correspond to the container accommodating part 2G, of the front surface part 2A and the rear surface part 2B. Thereby, a patient can grip the container 5 by each of the notch parts 2J for the pulling-out or the pushing-into.

The mouthpiece 3 is formed to protrude upward from the upper part of the body 2, that is, from the upper surface part 2E. The mouthpiece 3 is formed in an elongated, elliptic tubular shape in the left-right direction. As a result, the mouthpiece 3 can easily be held in the mouth without the mouth being widely opened. In addition, a passage area of the inhalation passage 4 to be described later can largely be formed in the mouthpiece 3.

The inhalation passage 4 is disposed to extend across the body 2 and the mouthpiece 3 in the upper-lower direction (axis line A direction). The inhalation passage 4 has a first end 4A on the lower side that is open to the ceiling surface 2H of the container accommodating part 2G. In addition, the inhalation passage 4 has a second end 4B on the upper side that is open to an upper end of the mouthpiece 3. The inhalation passage 4 is provided with a throttle part 4C on the first end 4A-side as the upstream side in a flowing direction of air. A passage area of the throttle part 4C is made smaller than that of the downstream side of the inhalation passage 4.

Thereby, when the inhalation passage 4 inhales air, a flow velocity of the air is made faster at the throttle part 4C, making it possible to enhance a suction force of the medical agent 6. In addition, the inhalation passage 4 is so configured that the passage area throttled at the throttle part 4C becomes an abruptly large passage area. In this case, the inhalation passage 4 can generate a turbulence flow by releasing a pressure of the air at once to disperse the medical agents 6 contained in the air finely.

The container 5 is accommodated in the container accommodating part 2G of the body 2. The container 5 is formed in such a shape as to be accommodated in the container accommodating part 2G to be movable in the left-right direction, specifically, is formed in a rectangular shape to be wide in width in the left-right direction and flat in the front-back direction. The container 5 has medical agent accommodating chambers 5A for accommodating the powdered medical agents 6 in two locations across the center part in the left-right direction. The two medical agent accommodating chambers 5A each have a lower side that is closed by a bottom part 5A1 and an upper side that is formed as an opening 5A2. The bottom part 5A1 is formed in a recessed, spherical shape. Thereby, the bottom part 5A1 can circulate and disperse the air having flowed thereinto in the medical agent accommodating chamber 5A from the opening 5A2.

In addition, the container 5 can move in the left-right direction in the container accommodating part 2G. Specifically the container 5 can be switched to positions between a dosing position (position as shown in FIG. 3) where the opening 5A2 of the medical agent accommodating chamber 5A that is one of the two medical agent accommodating chambers 5A is communicated with the throttle part 4C of the inhalation passage 4 and a storage position (position as shown in FIG. 1 and FIG. 2) where the openings 5A2 of both of the medical agent accommodating chambers 5A are separated from the throttle part 4C of the inhalation passage 4. In the dosing position of the container 5, the inflow passage 7 to be described later is communicated with the opening 5A2 of the medical agent accommodating chamber 5A that is one of the two medical agent accommodating chambers 5A.

The inflow passage 7 is positioned closer to the upper side than the container accommodating part 2G and is disposed on the body 2. The inflow passage 7 is composed of two inflow passages positioned across the inhalation passage 4. The inflow passage 7 has a first end 7A as an inlet port that is open to an exterior on the upper surface part 2E of the body 2. The inflow passage 7 has a second end 7B as an outlet port that is open toward the opening 5A2 of the medical agent accommodating chamber 5A disposed in the dosing position.

The two inflow passages 7 are arranged in a sharp, V-letter shape with the first ends 7A avoiding the mouthpiece 3 and being separated in the left-right direction and with the second ends 7B getting close to the throttle part 4C of the inhalation passage 4. Thereby, since an axis line B of the inflow passage 7 is positioned sharply to an axis line A of the inhalation passage 4, the air can be blown to the depth (bottom part 5A1) of the medical agent accommodating chamber 5A through the inflow passage 7. In addition, since the axis lines B of the inflow passages 7 intersect with each other, the air flowing out from the two inflow passages 7 collide with each other to generate a turbulence flow.

The two inflow passages 7 each are formed as a tapered passage, having a passage area getting smaller from the first end 7A toward the second end 7B. Accordingly, the inflow passage 7 can increase the velocity of the air flowing from the first end 7A toward the second end 7B. Thereby, the inflow passage 7 can swiftly inject out the air from the second end 7B toward the medical agent accommodating chamber 5A to curl up the medical agents 6. In addition, the inflow passage 7 swiftly injects out the air from the second end 7B, thereby making this air have directional characteristics. As a result, the inflow passage 7 can flow the air into the medical agent accommodating chamber 5A without flowing the air to the side of the inhalation passage 4 adjacent thereto.

Air holes 8 are disposed in a lower section of the mouthpiece 3. The Air holes 8 are disposed, for example, in two locations across the inhalation passage 4, that is, disposed to radially penetrate through the front part and the rear part of the mouthpiece 3. The air hole 8 is formed as a small-diameter hole for communication between an exterior of the mouthpiece 3 and the inhalation passage 4. When a patient breathes in in a state of holding the mouthpiece 3 in the mouth, the Air holes 8 can adjust the air to flow into the inhalation passage 4 from an exterior according to the lung capacity of the patient.

In detail, in a case where the lung capacity of a patient is large, when the patient breathes in in a state of holding the mouthpiece 3 in the mouth, the air can be flowed into the inhalation passage 4 through the Air holes 8. Thereby, difficulty in breathing at the dosing can be eliminated. On the other hand, in a case where the lung capacity of the patient is small, a flow amount of the air flowing into the inhalation passage 4 from the Air holes 8 can be limited by closing at least one of the two Air holes 8 with a fingertip. Thereby, the patient can efficiently inhale the air containing the medical agent 6 from the medical agent accommodating chamber 5A. It should be noted that the Air holes 8 may be configured to be disposed on the body 2. A closure preventive projection 8A raised in a semi-annular shape as to surround the air hole 8 is disposed in a position of an upper periphery of the air hole 8 in the mouthpiece 3. This closure preventive projection 8A is provided to prevent a patient from closing the air hole 8 unintentionally. On the other hand, the closure preventive projection 8A is raised to the degree that a patient can intentionally locate the position of the air hole 8 with the fingertip for closure. It should be noted that a shape of the closure preventive projection 8A may be, in addition to the semi-annular shape as described above, a reverse V-letter one, or raised portions linearly extending vertically in parallel with the air hole 8 on both sides of the air hole 8 in the left-right direction.

The medical agent inhaler 1 according to the present embodiment has the configuration as described above. Next, an explanation will be made of an operation at the time of inhaling the medical agent 6 accommodated in the medical agent accommodating chamber 5A of the container 5.

First, in the preparation operation, for example as shown in FIG. 3, the container 5 is moved in the right side relative to the body 2 to be disposed in the dosing position. At this time, the container 5 in the present embodiment is not provided with the air hole extending downward from the bottom part of the medical agent accommodating chamber to be open to the exterior as shown in Patent Documents 1 and 2. Accordingly, the container 5 in the present embodiment is configured to prevent the medical agent 6 accommodated in the medical agent accommodating chamber 5A from spilling out to the exterior.

When the container 5 is disposed in the dosing position, a patient inhales with the mouthpiece 3 held in the mouth. At this time, since the inhalation passage 4 and the medical agent accommodating chamber 5A are brought into negative pressure, the external air flows from the first end 7A to the second end 7B of the inflow passage 7. Because of this, the air injected out from the inflow passage 7 toward the opening 5A2 of the medical agent accommodating chamber 5A disperses the medical agents 6 in the medical agent accommodating chamber 5A to be mixed into the air. In addition, the air having contained the medical agent 6 is inhaled through the inhalation passage 4 to be administered to a patient. At the dosing, by selection between the opening and the closing of the two Air holes 8, the air to flow into the inhalation passage 4 can be adjusted according to the lung capacity.

Thus, according to the present embodiment, provided are: the body 2 that is provided with the container accommodating part 2G; the tubular mouthpiece 3 that protrudes upward from the upper part of the body 2; the inhalation passage 4 of which the first end 4A is open to the container accommodating part 2G and of which the second end 4B is open to the upper end of the mouthpiece 3; the container 5 that is accommodated in the container accommodating part 2G and is provided therein with the medical agent accommodating chamber 5A of which the lower side is closed and of which the upper side is formed as the opening 5A2, the container 5 being capable of switching positions between the dosing position where the opening 5A2 of the medical agent accommodating chamber 5A is communicated with the inhalation passage 4 and the storage position where the opening 5A2 of the medical agent accommodating chamber 5A is separated from the inhalation passage 4; and the inflow passage 7 that is disposed on the body 2 to be positioned closer to the upper side than the container accommodating part 2G, of which the first end 7A is open to the exterior and of which the second end 7B is open to the opening 5A2 of the medical agent accommodating chamber 5A disposed in the dosing position.

Accordingly, the container 5 in the present embodiment is not provided with the air hole extending downward from the bottom part of the medical agent accommodating chamber to be open to the exterior as shown in Patent Documents 1 and 2. As a result, since the medical agent 6 in the medical agent accommodating chamber 5A does not spill out to the exterior, a specific amount of the medical agents 6 accommodated in the medical agent accommodating chamber 5A can be administered to a patient to improve reliability on the medical agent inhaler 1.

Here, Patent Documents 1 and 2 are so configured that the air linearly flows from the air hole disposed in the bottom part of the medical agent accommodating chamber toward the inhalation passage. Therefore, in the medical agent accommodating chamber, the air just passes through the center section of the medical agents in a straight line and a great amount of the medical agents are left without being inhaled. However, the medical agent inhaler 1 of the present embodiment is configured to spray the air through the inflow passage 7 from the opening 5A2 of the medical agent accommodating chamber 5A. Thereby, since the medical agents 6 of the medical agent accommodating chamber 5A can effectively be dispersed by the air injected from the inflow passage 7, the medical agents 6 can be inhaled without being left.

The inflow passage 7 is composed of two inflow passages positioned across the inhalation passage 4. On top of that, since the two inflow passages 7 are arranged in a way that the axis lines B intersect with each other, the air flowing out from one of the two inflow passages 7 collides with the air flowing out from the other in the medical agent accommodating chamber 5A to generate the turbulence flow. Also thanks to this, the medical agents 6 in the medical agent accommodating chamber 5A can be dispersed to improve the inhalation efficiency.

In addition, the axis line B of the inflow passage 7 is disposed at a sharp angle to the axis line A of the inhalation passage 4. Because of this, the air injected out from the inflow passage 7 can be flowed to reach to the depth (bottom part 5A1) of the medical agent accommodating chamber 5A to disperse all the amounts of the medical agents 6 in the medical agent accommodating chamber 5A.

Further, the two inflow passages 7 are formed as tapered passages, each having a passage area getting smaller from the first end 7A toward the second end 7B. Accordingly, the inflow passage 7 swiftly injects out the air at a high velocity, thereby making it possible to make this injected air have directional characteristics. As a result, the air injected out from the inflow passage 7 can flow into the medical agent accommodating chamber 5A without flowing to the side of the inhalation passage 4 adjacent thereto. Also because of this, the medical agents 6 in the medical agent accommodating chamber 5A can be dispersed.

On the other hand, the air hole 8 is disposed in the lower section of the mouthpiece 3 to adjust the air flowing into the inhalation passage 4 from the exterior. Accordingly, the air hole 8 can adjust the air to flow into the inhalation passage 4 from the exterior according to the lung capacity of a patient when the patient breathes in with the mouthpiece 3 held in the mouth, thus eliminating the difficulty in breathing at the dosing.

Figure 4:
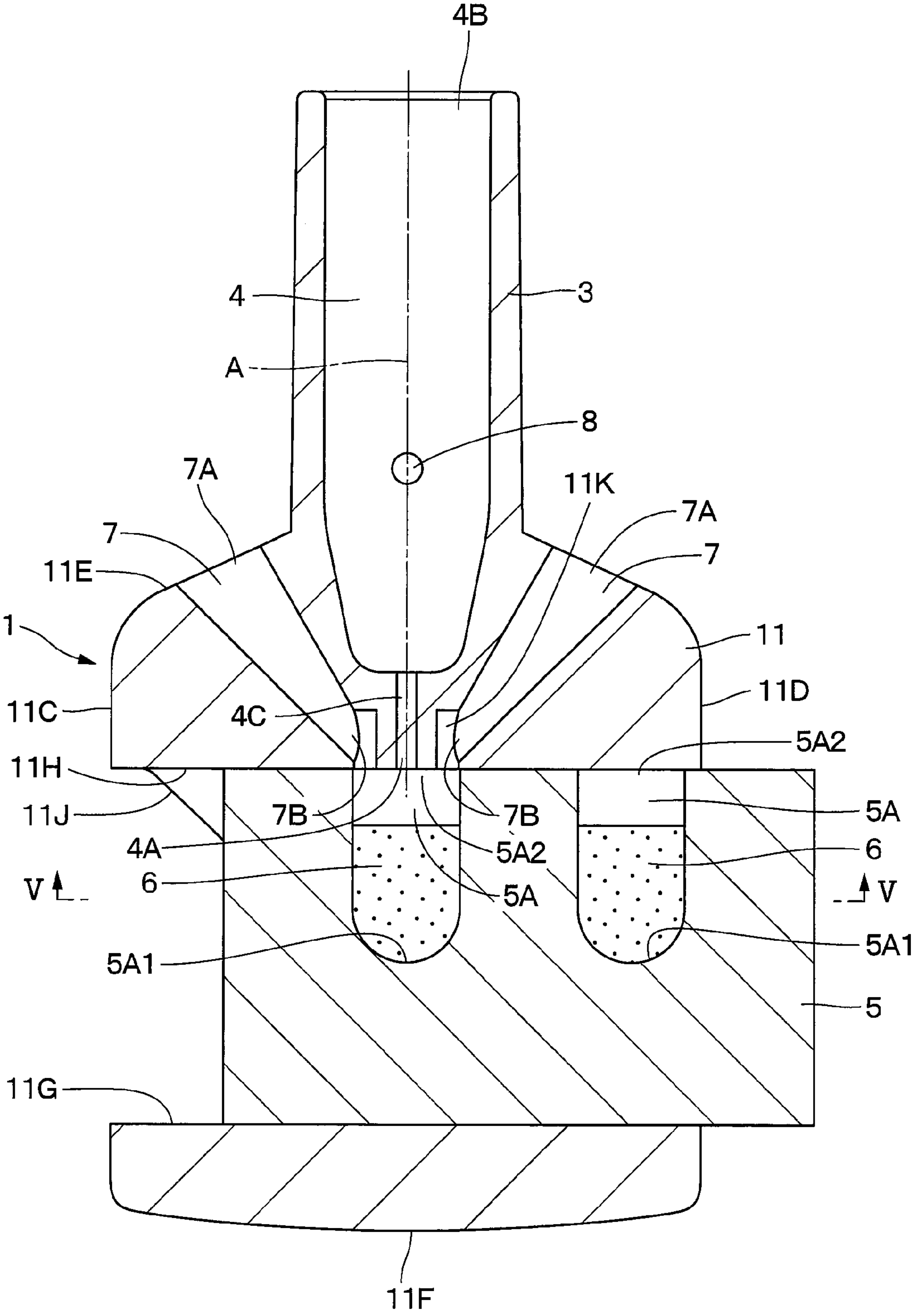
FIG. 4 is a cross section showing a medical agent inhaler provided with a body according to a second embodiment of the present invention.
Figure 5:
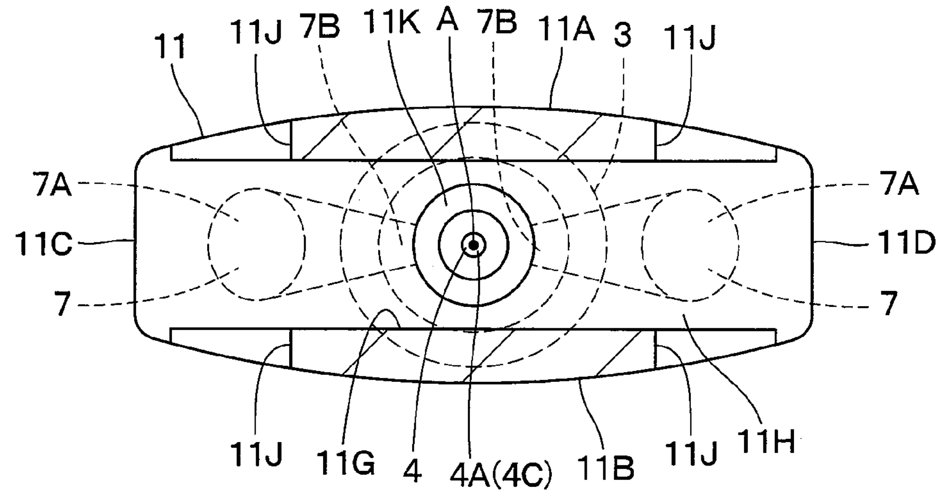
FIG. 5 is a cross section showing the body and the like, as viewed from an arrow V-V direction in FIG. 4.

Next, FIG. 4 and FIG. 5 show a second embodiment of the present invention. The present embodiment is characterized in that a body is provided with an annular space that is disposed in a position of surrounding a first end of an inhalation passage to be open toward an opening of a medical agent accommodating chamber disposed in a dosing position, and a second end of an inflow passage is communicated with the annular space. It should be noted that in the second embodiment, components identical to those in the first embodiment are referred to as identical reference numerals and an explanation thereof is omitted.

In FIG. 4, a body 11 according to the second embodiment has, as similar to the body 2 according to the first embodiment, a front surface part 11A, a rear surface part 11B, a left surface part 11C, a right surface part 11D, an upper surface part 11E, a lower surface part 11F, a container accommodating part 11G, a ceiling surface 11H and a notch part 11J. However, the body 11 according to the second embodiment differs in a point where an annular space 11K is disposed in a position of surrounding the first end 4A (throttle part 4C) of the inhalation passage 4 from the body 2 according to the first embodiment.

The annular space 11K is open toward the opening 5A2 of a medical agent accommodating chamber 5A disposed in a dosing position. In detail, as shown in FIG. 5, the annular space 11K is formed as a cylindrical space surrounding the throttle part 4C of the inhalation passage 4. On top of this, second ends 7B of two inflow passages 7 are communicated with the annular space 11K to oppose to each other toward an axis line A of the inhalation passage 4.

Thereby, the air having flowed into the annular space 11K from the inflow passage 7 is injected out toward an outer peripheral section of the medical agent accommodating chamber 5A from the annular space 11K. A cylindrical air flow injected out from the annular space 11K can disperse the entirety of the medical agents 6 in the medical agent accommodating chamber 5A.

In this way, also in the second embodiment as configured thus, functional effects as substantially similar to the first embodiment as described above can be obtained. Particularly, according to the second embodiment, since the annular space 11K can form the cylindrical air flow directed to the outer peripheral section of the medical agent accommodating chamber 5A, the medical agents 6 can effectively be dispersed.

Figure 6:
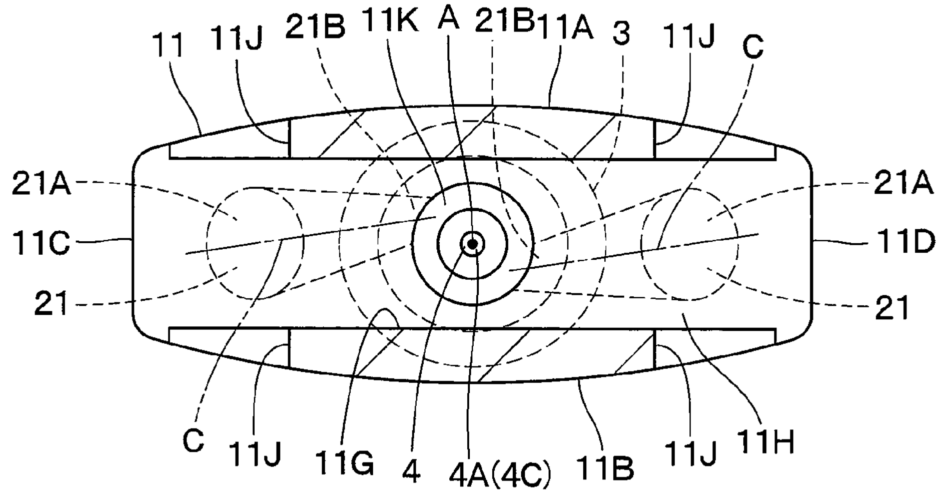
FIG. 6 is a cross section showing a medical agent inhaler provided with an inflow passage according to a third embodiment of the present invention, as viewed from the same position as in FIG. 5.

Next, FIG. 6 shows a third embodiment of the present invention. The present embodiment is characterized in that a second end of an inflow passage is open to a position deviating from an axis line of an inhalation passage. It should be noted that in the third embodiment, components identical to those in the second embodiment are referred to as identical reference numerals and an explanation thereof is omitted.

In FIG. 6, an inflow passage 21 according to the third embodiment comprises, as similar to the inflow passages 7 according to the second embodiment, two inflow passages forming a sharp V-letter shape in positions across an inhalation passage 4. In addition, the inflow passage 21 is formed as a tapered passage of which a passage area becomes smaller from a first end 21A toward a second end 21B. However, the two inflow passages 21 according to the third embodiment differ in a point where the second ends 21B are open to positions deviating from an axis line A of the inhalation passage 4 from the inflow passages 7 according to the second embodiment.

The two inflow passages 21 are arranged obliquely so that axis lines C radially deviate from the axis line A of the inhalation passage 4. Thereby, the second ends 21B of the two inflow passages 21 are respectively communicated with an annular space 11K at the opposite sides across the axis line A of the inhalation passage 4.

Thereby, the air flowing into the annular space 11K from the inflow passages 21 forms a swirl flow in the annular space 11K. This swirl flow can disperse the entirety of the medical agents 6 in the medical agent accommodating chamber 5A.

In this way, also in the third embodiment as configured thus, functional effects as substantially similar to each of the embodiments as described above can be obtained.

Particularly, according to the third embodiment, since the two inflow passages 21 can inject out the swirl air flow toward the medical agent accommodating chamber 5A, the medical agents 6 can be dispersed more effectively.

Next, aspects of medical agent inhalers to be described as follows will be considered as the medical agent inhalers included in the above-mentioned embodiments.

A first aspect of the medical agent inhaler is characterized by including a body that is provided therein with a container accommodating part, a tubular mouthpiece that protrudes upward from an upper part of the body, an inhalation passage of which a first end is open to the container accommodating part and of which a second end is open to an upper end of the mouthpiece, a container that is accommodated in the container accommodating part and is provided therein with a medical agent accommodating chamber of which a lower side is closed and of which an upper side is formed as an opening, the container being capable of switching positions between a dosing position where the opening of the medical agent accommodating chamber is communicated with the inhalation passage and a storage position where the opening of the medical agent accommodating chamber is separated from the inhalation passage, and an inflow passage that is disposed on the body to be positioned closer to the upper side than the container accommodating part, of which a first end is open to an exterior and of which a second end is open toward the opening of the medical agent accommodating chamber disposed in the dosing position.

A second aspect of the medical agent inhaler is characterized in that in the first aspect, an air hole is disposed in at least one of the body and the mouthpiece for communication between the exterior and the inhalation passage.

A third aspect of the medical agent inhaler is characterized in that in the first aspect and in the second aspect, the inflow passage is formed as a tapered passage of which a passage area reduces from the first end toward the second end.

A fourth aspect of the medical agent inhaler is characterized in that in any of the first aspect to the third aspect, the inflow passage comprises two inflow passages arranged in positions across the inhalation passage.

A fifth aspect of the medical agent inhaler is characterized in that in any of the first aspect to the fourth aspect, the body is provided with an annular space that is disposed in a position of surrounding the first end of the inhalation passage to be open toward the opening of the medical agent accommodating chamber disposed in the dosing position, wherein the second end of the inflow passage is communicated with the annular space.

A sixth aspect of the medical agent inhaler is characterized in that in any of the first aspect to the fifth aspect, the second end of the inflow passage is open in a position deviating from an axis line of the inhalation passage.

DESCRIPTION OF REFERENCE NUMERALS

1: MEDICAL AGENT INHALER
2, 11: BODY
2E, 11E: UPPER SURFACE PART (UPPER SIDE)
2G, 11G: CONTAINER ACCOMMODATING PART
3: MOUTHPIECE
4: INHALATION PASSAGE
4A, 7A, 21A: FIRST END
4B, 7B, 21B: SECOND END
5: CONTAINER
5A: MEDICAL AGENT ACCOMMODATING CHAMBER
5A2: OPENING
6: MEDICAL AGENT
7, 21: INFLOW PASSAGE
8: AIR HOLE
11K: ANNULAR SPACE
A: AXIS LINE OF INHALATION PASSAGE
C: AXIS LINE OF INFLOW PASSAGE

The invention claimed is:

1. A medical agent inhaler comprising:
a body that is provided therein with a container accommodating part;
a tubular mouthpiece that protrudes upward from an upper part of the body;
an inhalation passage of which a first end is open to the container accommodating part and of which a second end is open to an upper end of the mouthpiece;
a container that is accommodated in the container accommodating part and is provided therein with a medical agent accommodating chamber of which a lower side is closed and of which an upper side is formed as an opening, the container being capable of switching positions between a dosing position where the opening of the medical agent accommodating chamber is communicated with the inhalation passage and a storage position where the opening of the medical agent accommodating chamber is separated from the inhalation passage;
and an inflow passage that is disposed on the body to be positioned closer to the upper side than the container accommodating part, of which a first end is open to an exterior and of which a second end opens directly into the opening of the medical agent accommodating chamber disposed in the dosing position, wherein
the inhalation passage is provided with a throttle part on the first end of the inhalation passage,
the inflow passage is provided such that an axis line of the inflow passage is straight,
the inflow passage is formed as a tapered passage of which a passage area reduces from the first end toward the second end, and
the second end of the inflow passage is radially closer to the throttle part than the first end of the inflow passage.

2. The medical agent inhaler according to claim 1, wherein the body is provided with an annular space that is disposed in a position of surrounding the first end of the inhalation passage to be open toward the opening of the medical agent accommodating chamber disposed in the dosing position, wherein the second end of the inflow passage is communicated with the annular space.

3. The medical agent inhaler according to claim 2,
wherein an outer diameter of the annular space and an outer diameter of the opening of the medical agent accommodating chamber are the same and have the same shape.

4. The medical agent inhaler according to claim 1, wherein the second end of the inflow passage is open in a position deviating from an axis line of the inhalation passage.

5. The medical agent inhaler according to claim 1,
wherein the inflow passage is formed as the axis line of the inflow passage touches an upper surface of the medical agent accommodated in the medical agent accommodating chamber.

6. The medical agent inhaler according to claim 5,
wherein the inflow passage comprises two inflow passages arranged in positions across the inhalation passage.

7. The medical agent inhaler according to claim 1, wherein the lower side of the medical agent accommodating chamber is closed when the container is in both the dosing position and the storage position.

8. The medical agent inhaler according to claim 1, wherein the second end opening of the inflow passage into the medical agent accommodating chamber is separated from the first end opening of the inhalation passage into the medical agent accommodating chamber such that the second end opening of the inflow passage directly communicates with the medical agent accommodating chamber when in the dosing position.

* * * * *